(12) United States Patent
Noguchi et al.

(10) Patent No.: US 6,355,256 B1
(45) Date of Patent: Mar. 12, 2002

(54) COMPOSITIONS CONTAINING A P53 DERIVED PROTEIN OR PEPTIDE, AN ADJUVANT, AND INTERLEUKIN-12 AND USES THEREOF

(75) Inventors: Yuji Noguchi; Yao-tseng Chen; Lloyd J. Old, all of New York, NY (US)

(73) Assignees: Ludwig Institute for Cancer Research; Memorial Sloan Kettering Cancer Center, both of New York, NY (US)

( * ) Notice: Subject to any disclaimer, the term of this patent is extended or adjusted under 35 U.S.C. 154(b) by 0 days.

(21) Appl. No.: 08/408,915

(22) Filed: Mar. 22, 1995

Related U.S. Application Data

(63) Continuation-in-part of application No. 08/316,622, filed on Sep. 30, 1994, now abandoned.

(51) Int. Cl.[7] .................. A61K 39/00; A61K 49/00; A61K 39/38; A61K 45/00
(52) U.S. Cl. ................ 424/277.1; 424/9.1; 424/9.2; 424/85.2; 424/184.1; 424/278.1; 424/279.1
(58) Field of Search ................ 424/277.1, 85.2, 424/279.1, 9.1, 9.2, 184.1, 278.1

(56) References Cited

U.S. PATENT DOCUMENTS 5,057,540 A   10/1991   Kensil et al. .................. 514/25

FOREIGN PATENT DOCUMENTS

| WO | WO9219758 | | 11/1992 |
|----|-----------|--|---------|
| WO | WO94/02167 | * | 2/1994 |
| WO | WO 94/16716 | * | 8/1994 |

OTHER PUBLICATIONS

Nijman et al, Immunol. Lett., 40(2):171–178, 1994 (may).*

Nastala et al, J. Immunol, 153(4):1697–1706, 1994 (Aug.).*

Livingston P.O., Curr. Opin. Immunol., 4(5):624–629, 1992.*

Hall S.S., Science, 263(5154):1685–1686, 1994 (Mar.).*

Hall, "IL–12" at the Crossroads, Science 268: 1432–1434 (Jun. 9, 1995).

* cited by examiner

*Primary Examiner*—Rodney P Swartz
(74) *Attorney, Agent, or Firm*—Fulbright & Jaworski, LLP

(57) ABSTRACT

The invention involves the combination of Interleukin-12 with p53 derived peptides and an adjuvant, preferably QS-21. It is found that this combination provokes a surprisingly strong immune response. Further, in an accepted in vivo model, the use of compositions containing these three ingredients led to diamatic decreases in the growth of induced tumors, thus suggesting a therapeutic regime.

10 Claims, 5 Drawing Sheets

SEQUENCE LISTING (1) GENERAL INFORMATION:

(iii) NUMBER OF SEQUENCES: 2

-continued (2) INFORMATION FOR SEQ ID NO: 1:

(i) SEQUENCE CHARACTERISTICS:
        (A) LENGTH:  9 amino acids
        (B) TYPE:    amino acid
        (D) TOPOLOGY: linear (xi) SEQUENCE DESCRIPTION: SEQ ID NO: 1:

Lys Tyr Ile Cys Asn Ser Ser Cys Met
            5

(2) INFORMATION FOR SEQ ID NO: 2:

(i) SEQUENCE CHARACTERISTICS:
        (A) LENGTH:  9 amino acids
        (B) TYPE:    amino acid
        (D) TOPOLOGY: linear (xi) SEQUENCE DESCRIPTION: SEQ ID NO: 2:

Lys Tyr Met Cys Asn Ser Ser Cys Met

COMPOSITIONS CONTAINING A P53 DERIVED PROTEIN OR PEPTIDE, AN ADJUVANT, AND INTERLEUKIN-12 AND USES THEREOF

RELATED APPLICATION

This application is a continuation-in-part of patent application Ser. No. 08/316,622, filed on Sep. 30, 1994 now abandoned.

FIELD OF THE INVENTION

This invention relates to compositions useful in the generation of an immune response. The immune response includes, inter alia, provocation of T cells, such as cytolytic T cells, against complexes of a p53 derived peptide and MHC molecules or a p53 derived peptide or protein itself, as well as antibodies against such peptides and proteins. Such T cells and antibodies may be generated, e.g., in a mouse, rat, rabbit, sheep, goat or other non-human animal, and then used in diagnostic methods to identify tumor presence. They may also be generated in vitro such as by cell culture and hybridoma techniques. The compositions may also be used, therapeutically, via administration to a subject afflicted with a cancerous condition or one where cell transformation has taken place, to provoke an immune response against tumors, cancer cells, and transformed cells.

BACKGROUND AND PRIOR ART

Adjuvants, broadly defined, are substances which promote immune responses. Frequently, the adjuvant of choice is Freund's complete adjuvant, or killed *B. pertussis* organisms, used in combination with alum precipitated antigen. A general discussion of adjuvants is provided in Goding, Monoclonal Antibodies:

Principles & Practice (Second edition, 1986), at pages 61–63, which are incorporated by reference herein. Goding notes, however, that when the antigen of interest is of low molecular weight, or is poorly immunogenic, coupling to an immunogenic carrier is recommended. Such molecules, according to Goding, generally have molecular weights below about 1000. Among the carriers suggested by Goding, at page 283, are keyhole limpet hemocyanin, bovine serum albumin, ovalbumin, and fowl immunoglobulin.

What is problematic about such carriers, however, is that frequently they are also immunogenic themselves. Thus, the immune response may be a general one, with part, most, or all of it being directed against the carrier molecule rather than the immunogen itself.

Exemplary of developments in the art as they relate to adjuvants is U.S. Pat. No. 5,057,540 to Kensil, et al, the disclosure of which is incorporated by reference herein. Kensil et al disclose the preparation of various saponin extracts, which are useful as adjuvants in immunogenic compositions. As they are natural products, the extracts are not completely defined. Kensil, et al do provide a complete and enabling disclosure for how various extracts, including QA-7, QA-19, and QA-21 (also referred to as QS-21) are prepared. Experiments are set forth in which bovine serum albumin ("BSA") was combined with various extracts (examples 8 and 9), and where feline leukemia virus recombinant glycoprotein "gp70RΔ was tested, following absorption to aluminum hydroxide (alum). The two immunogens tested, however, are expected to be immunogenic in their own right (gp7 ORΔ has a molecular weight of 70 kd, and serum albumin has about the same molecular weight). No experiments were carried out at all on molecules which should, per se, be considered to be poorly or even non-immunogenic, and thus would be expected to require the use of alum absorption or the use of haptenic carriers for provocation of a response.

In PCT Application WO9219758, which corresponds to defensive publication 7697275, which is incorporated by reference herein, an adjuvant referred to as "MTP-MF59" is disclosed. This adjuvant is used in connection with a *Plasmodium falciparum* protein, "Pfs-25-B". This combination is described as a transmission blocking vaccine. The *P. falciparum* protein is itself large enough to be immunogenic. Thus, none of the art shows that the improved adjuvants can be used in combination with presumptively non-immunogenic proteins and peptides to yield immunologically effective compositions.

Interleukin-12, or "IL-12" hereafter, is known to play an important role in the differentiation of $T_H0$-$T_H1$, and $T_H2$-$T_H0$ cells in vivo. See Manetti, et al, J. Exp. Med 177:1199–1204 (1993); Hsieh, et al, Science 260:547–549 (1993).

The molecule referred to as p53 has been known for a number of years. A brief summary of the molecule is provided by Culotta, et al., Science 262: 1958–1961 (1993) ("p53 Sweeps Through Cancer Research"). As reported therein, about 50% of all subjects diagnosed with cancer have a p53 mutation (or p53 mutations). These mutations can abolish the function of normal, or wild type p53, which is to act as a tumor suppressor of the observed mutations, about 90% involve a change in amino acid sequence (a "missense" mutation), as compared to "nonsense" mutations, where the changes in the gene result in truncation or destabilization of the protein. The wild type p53 molecule is also involved in the cell cycle, in that it inhibits cell division. This is accomplished by activating a second protein of 21 kilodaltons, which inhibit the proteins "cdk" and "cyk", which are required for cell division.

It has now been found, surprisingly, that compositions can be made which comprise immunogenic peptides, such as p53 derived peptides, in combination with an adjuvant such as those described above and the cytokine interleukin-12, or "IL-12". When administered to a subject animal, these compositions provoke an immunogenic response which is surprisingly strong, and totally unexpected in view of the response elicited with each element by itself, or pairs of these elements. In especially preferred embodiments the immunogenic peptide or protein is combined with the adjuvant QS21, which is disclosed in the Kensil, et al, patent, incorporated by reference supra.

A further aspect of this invention is the use of the cytokine, IL-12. Other interleukins, i.e., IL-1, IL-2, IL-3, IL-4, IL-5, IL-6, IL-7, IL-8, IL-9, IL-10, and IL-11, may also be used in view of their known efficacy as T-cell and B-cell growth factors. Of these, IL-2 is especially preferred. The compositions yield unexpected results when administered to T cells or B cells, in vitro or in vivo, in that their proliferation or other response, is surprisingly enhanced.

The immunogens of this invention include all p53 derived peptides and proteins, such as mutant p53 peptides, as exemplified.

The invention is described in greater detail in the disclosure which follows.

BRIEF DESCRIPTION OF THE FIGURES

In FIG. 2A, IL-12 was administered 14 days before challenge with Meth A cells. In FIG. 2B, the IL-12 was administered on the same day that the challenge took place. In FIG. 2C, the IL-12 was administered 7 days after challenge.

In FIGS. 3A–3E, QS-21 was used. In FIGS. 3F–3J, IFA was used. As explained infra, various doses of IL-12 were used.

In FIG. 4A, the mutant peptide was administered in QS-21. In FIG. 4B, wild type peptide was combined with QS-21, and in FIG. 4C, QS-21 was used alone. The peptide/adjuvant combination was administered 7 and 14 days after challenge with Meth A cells. A very low dose of IL-12 (1 ng) was administered at day 7, and then as elaborated upon infra.

DETAILED DESCRIPTION OF PREFERRED EMBODIMENTS

Example 1

The anti-tumor effect of IL-12, used in combination with mutant p53 peptides, was studied.

The in vivo model employed used the transplantable, methylcholanthrene-induced sarcoma "Meth A." This is a sarcoma of BALB/C (murine) origin, passaged as an ascitic tumor. See Old, et al, Ann. N.Y. Acad. Sci 101:80–106 (1962), incorporated by reference in its entirety.

BALB/C female mice were injected intradermally with $5 \times 10^4$ Meth A cells on day 0. Seven days later, a treatment regime began, wherein the animals received doses of IL-12, 4 times a week. Control animals received no IL-12. The remaining animals received 1 ng, 10 ng, 100 ng, or 500 ng of IL-12 in each dose, administered by intraperitoneal injection.

The effect of the IL-12 on the induced tumors was observed by measuring the diameter of the tumors at the end of the treatment period. FIGS. 1A, 1B, 1C, 1D and 1E show this. The panels show results with doses of 0 ng, 1 ng, 10 ng, 100 ng, and 500 ng, respectively.

It is clear from these figures that there is a dose dependent anti-tumor effect provoked by IL-12, although the doses are extremely small.

The effect of the IL-12 was abolished by administering monoclonal antibodies against CD8 molecules, but was not affected via administration of anti-CD4 mAbs. This suggests that cytolytic T cells are an essential part of the response.

Example 2

Figure 1A:
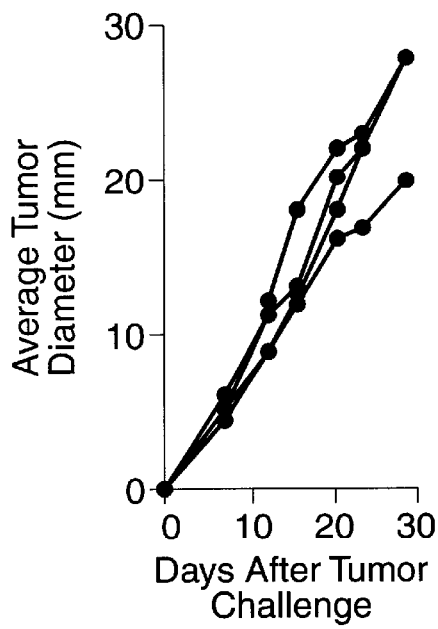
FIGS. 1A–1E, inclusive, depict experiments showing the antitumor effect of IL-12. In these figures, differing doses of IL-12 were administered to mice which had been injected with Meth A sarcoma cells.
Figure 1B:
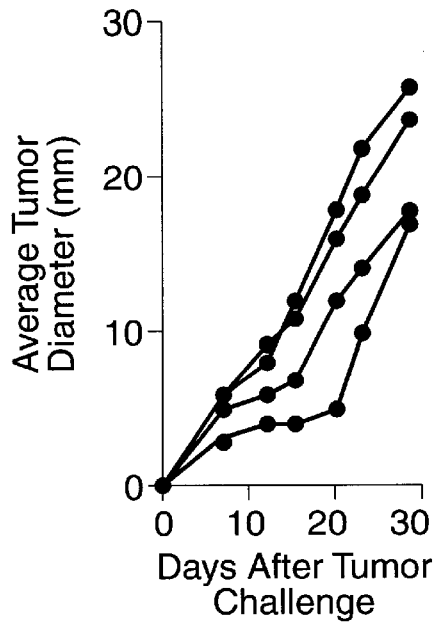
Figure 1C:
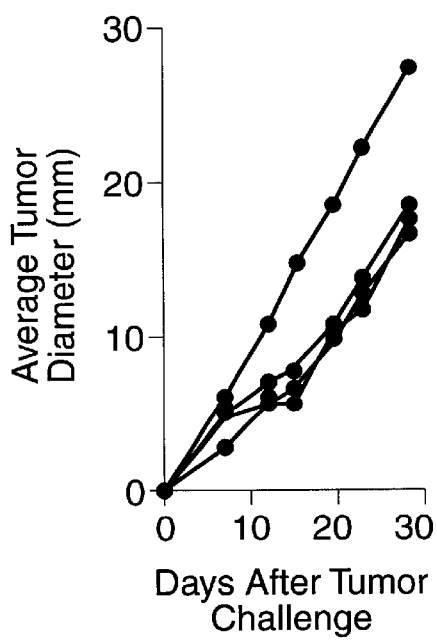
Figure 1D:
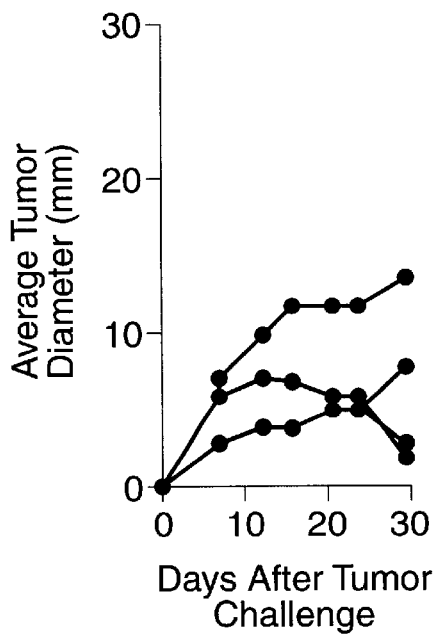
Figure 1E:
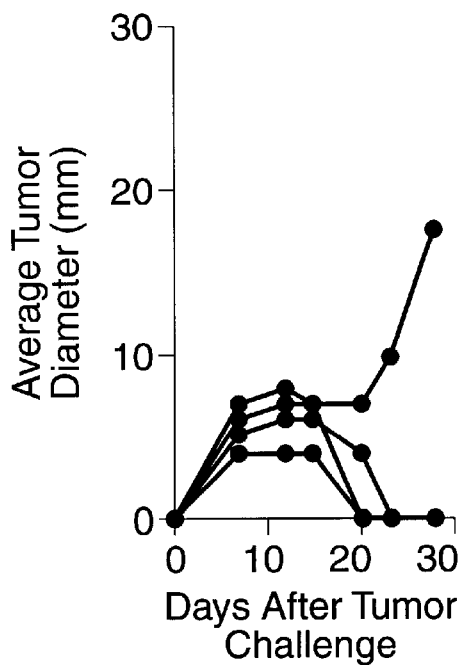
Figure 2A:
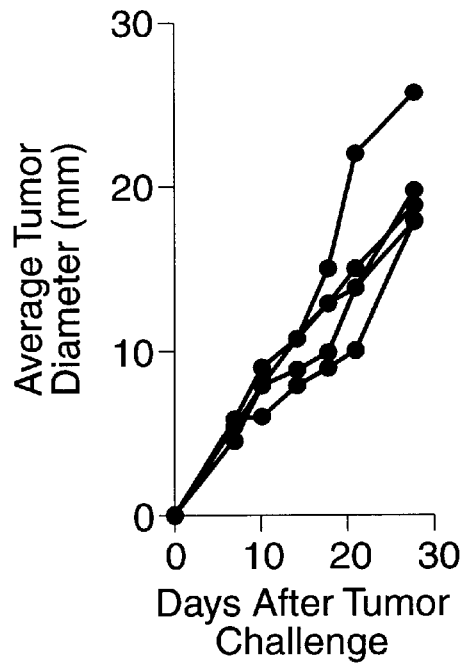
FIGS. 2A–2C show the importance of the timing of the administration of IL-12.
Figure 2B:
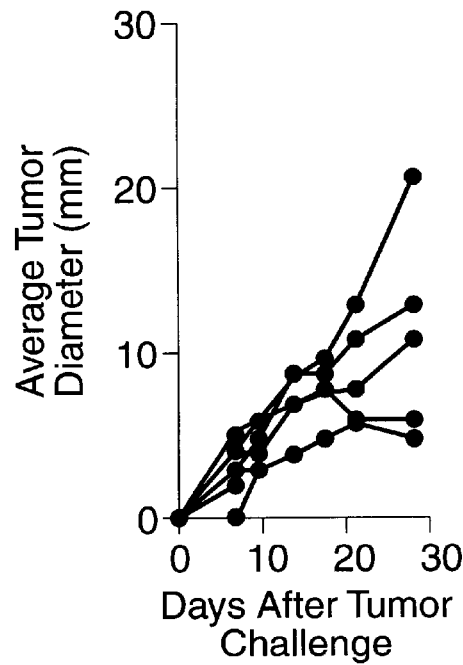
Figure 2C:
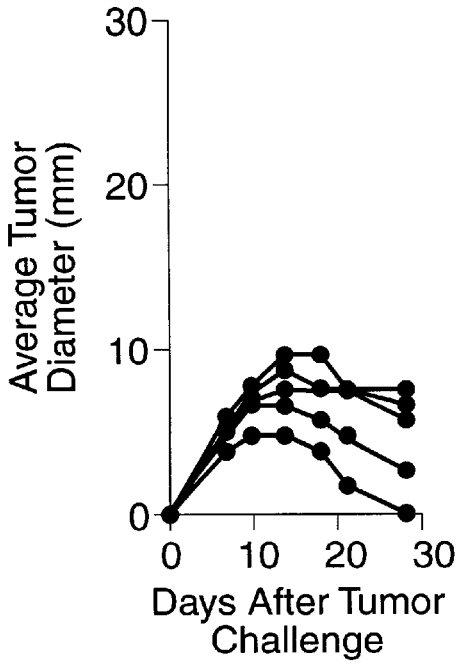

The importance of timing in the administration of IL-12 was then studied. In these experiments, female BALB/C mice were again injected with $5 \times 10^4$ Meth A cells, as in Example 1 (day 0). Injections of 100 ng IL-12 were administered at day "−14" (i.e., 14 days before challenge with the tumor cells), day 0, or day 7 (i.e., 7 days after challenge) as in Example 1. These results, presented in FIGS. 2A (day "−14"), 2B (day 0), and 2C (day 7) show that IL-12 is most effective after the tumor had become established.

Example 3

The experiments set forth in this example evaluate the effect of IL-12 on generation of cytolytic T cells ("CTLs" hereafter) specific to peptide/MLTC complexes.

Peptide 234 CM has amino acid sequence:

Lys Tyr Ile Cys Asn Ser Ser Cys Met (SEQ ID NO: 1) and contains a point mutation in codon 234 of Meth A p53. The wild type counterpart is Lys Tyr Met Cys Asn Ser Ser Cys Met (SEQ ID NO: 2) BALB/C female mice were immunized with 100 μg of the wild type peptide, combined with the adjuvant QS-21, described supra, or Incomplete Freund's Adjuvant ("IFA"). A total of 10 μg of QS-21 was used for each injection. The IFA was dissolved in PBS, at concentrations of 1 mg/ml. The combination of peptide and adjuvant was administered twice at weekly intervals. Over the two week period, the animals were also injected with IL-12, four times. The dose of IL-12 was either 0.1 ng, 1 ng, 10 ng, or 100 ng. Control animals received no IL-12.

One week after the last injections, the spleen cells of the immunized mice were sensitized with syngeneic spleen cells, pulsed with the mutant peptide (234CM). Sensitization was carried out using well known techniques. The activity of CTLs in the sample was determined using the well known $^{51}$Cr release assay. This methodology is described by Noguchi, et al, Proc. Natl. Acad. Sci USA 91:3171–3175 (1994), incorporated by reference. Sensitization with pulsed spleen cells is a methodology which leads to a much stronger response than if peptide alone were administered.

Figure 3A:
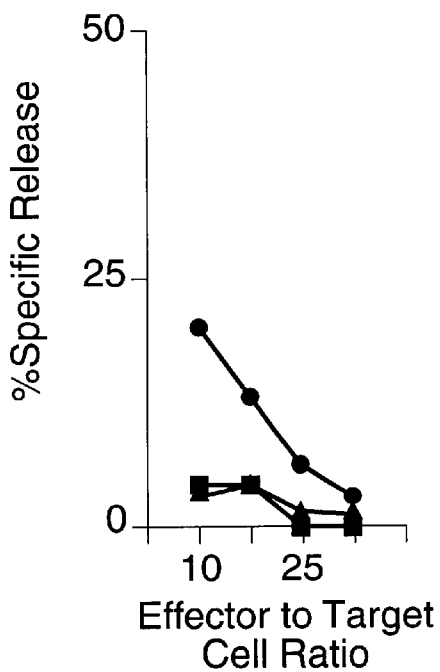
FIGS. 3A–3J cover the use of two adjuvants, QS-21 and Incomplete Freund's adjuvant, together with IL-12. The experiments are directed to the study of IL-12's immuno modulatory effect.
Figure 3B:
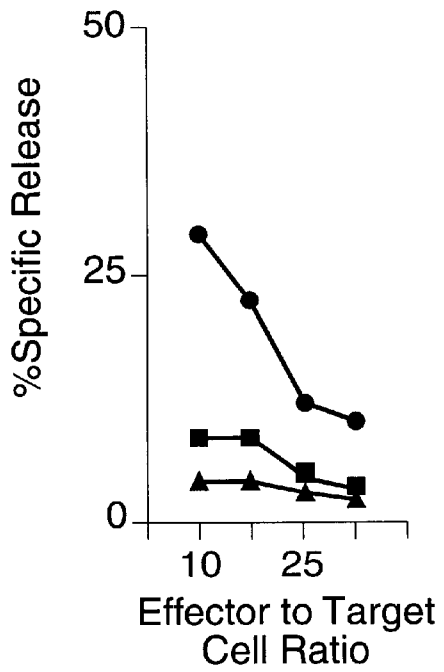
Figure 3C:
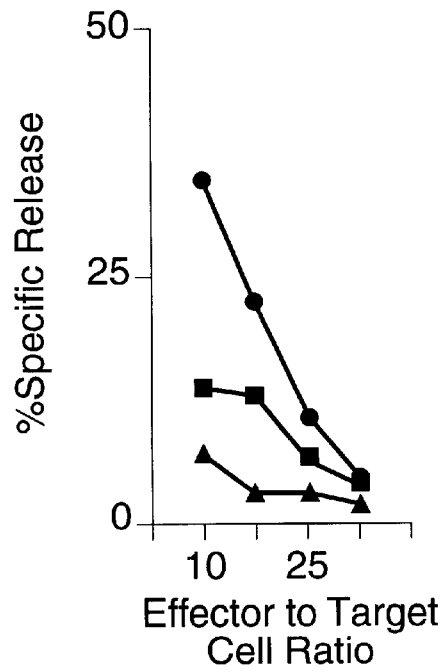
Figure 3D:
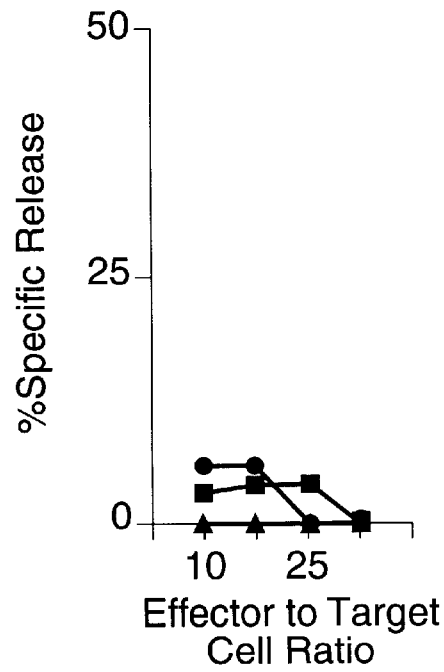
Figure 3E:
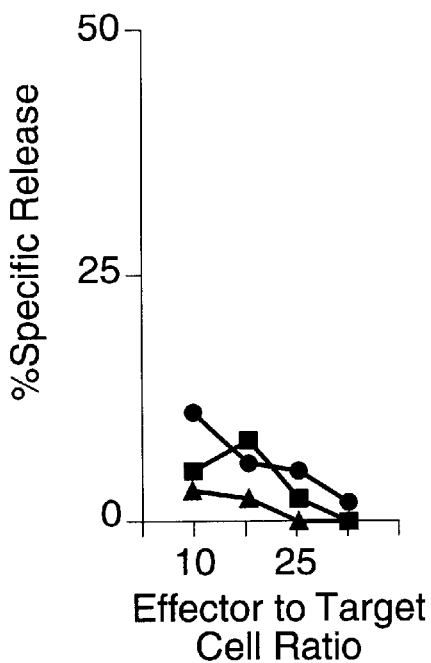
Figure 3F:
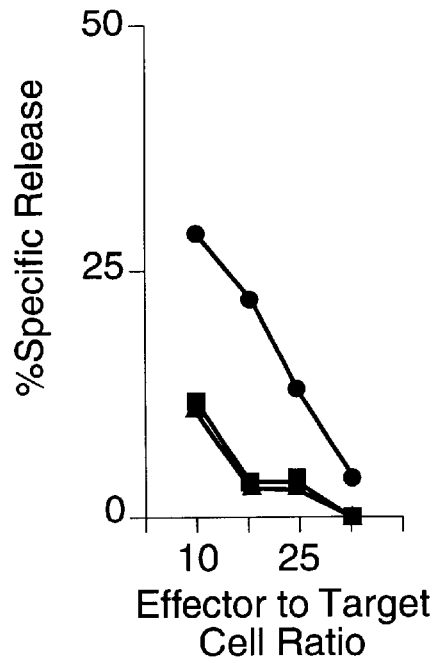
Figure 3G:
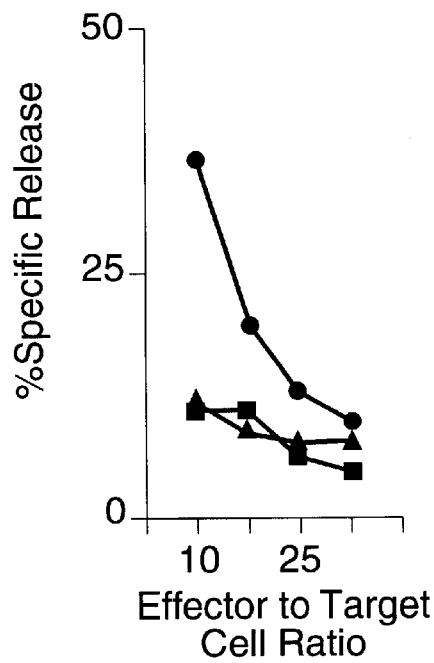
Figure 3H:
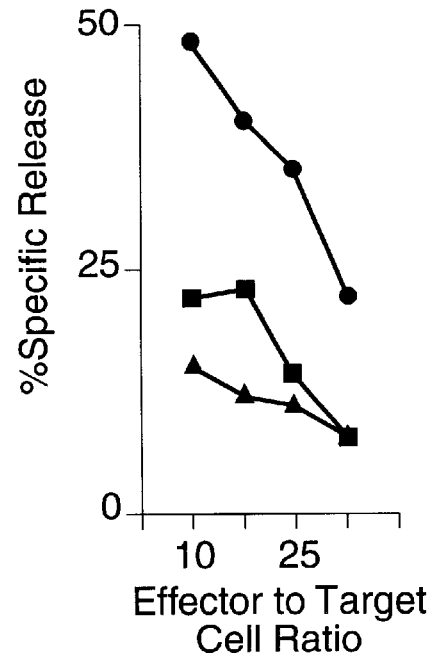
Figure 3I:
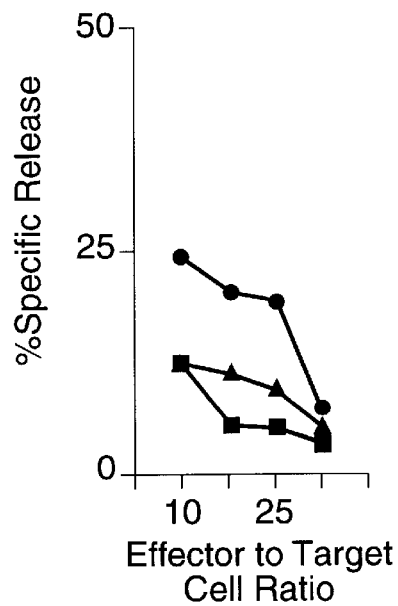
Figure 3J:
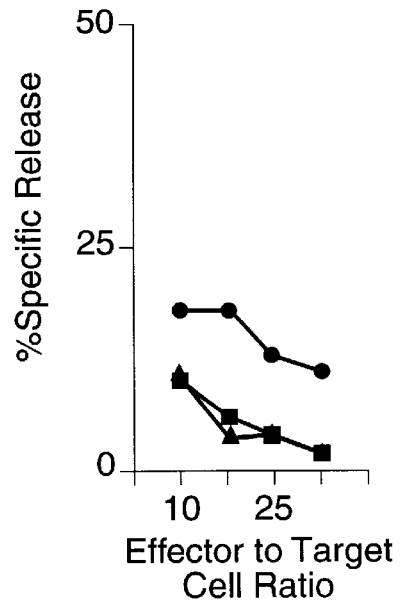

The results are presented in FIG. 3, where FIGS. 3A and 3F present data from controls, FIGS. 3B and 3G show the data obtained when 0.1 ng of IL-12 was used, FIGS. 3C and 3H show results where 1 ng of IL-12 was used, FIGS. 3D and 3I present the results where 10 ng of the cytokine were used, and 3E and 3J, where 100 ng were used. Data are presented in terms of the percentage of chromium release, where the amount of peptide contacted to the cells was 2.5 μg or 10 μg, FIGS. 3A–3E are from experiments in which QS-21 was used, while FIGS. 3F–3J resulted from experiments where IFA was used.

In FIGS. 3A–3J, the filled in dots (●—●) represent the data from the mutant peptide experiments. Also presented are results in which the wild type peptide was pulsed to cell line P1-HTR (a cell line derived from the mastocytoma P815, of DBA/2 origins. (See Old, et al, supra). These data are filled in squares (■—■). Also presented are data where P1-HTR were pulsed in the absence of peptide (▼—▼). This model is used, and is useful because one of the known features of Meth A is that it does not generate a CTL response. P1-HTR, however, does, and can be used as a model to determine the efficacy of the compositions discussed herein.

The data presented in FIG. 3 show that 1 ng of IL-12 was the optimal dose for the generation of CTLs, while higher doses had a suppressive effect. No CTLs were elicited following immunization with wild type peptide, regardless of the adjuvant or treatment with IL-12.

Example 4

This set of experiments investigated whether the combination of a peptide immunogen and a low dose of IL-12 would suppress the growth of established tumors.

As with the prior experiments, female BALB/C mice were injected with $5 \times 10^4$ Meth A cells at day 0. The mice received two injections of the mutant peptide in QS-21, the wild type peptide in QS-21, or QS-21 alone in the same manner described in Example 3, at weekly intervals. At day 7, the mice began receiving injections of 1 ng of IL-12 (4 times a week, for two weeks).

Figure 4A:
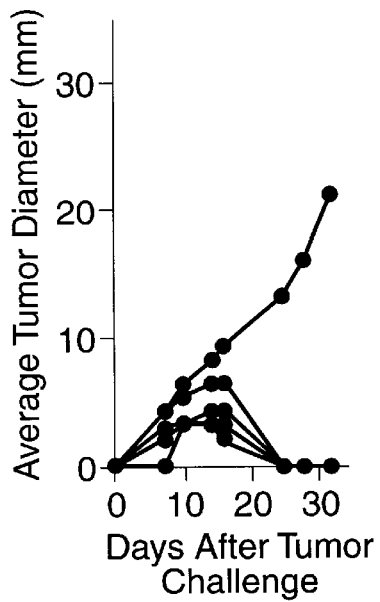
FIGS. 4A–4C show that there was strong suppression of tumor growth when low doses of IL-12 were administered with peptides.
Figure 4B:
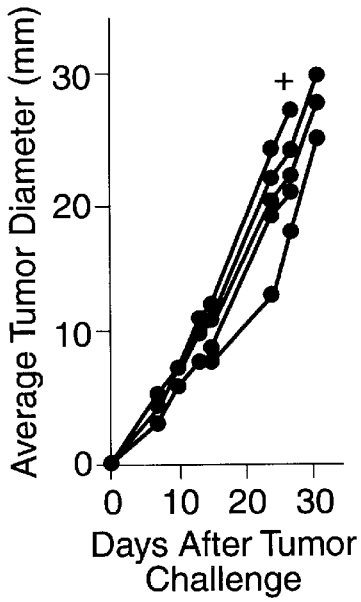
Figure 4C:
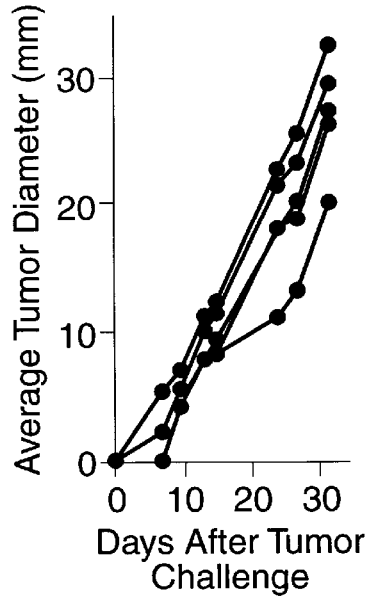

The results are presented in FIGS. 4A–4C. FIG. 4A resulted from QS-21 plus the mutant peptide followed by injections of IL-12. FIG. 4B resulted from QS-21 plus peptide, followed by injections with IL-12. FIG. 4C resulted from QS-21 alone followed by injections of IL-12. These figures show that the IL-12 had a growth suppressive effect on the tumors. In results not depicted, immunization with wild type peptide did not lead to suppression of tumor growth, even when combined with QS-21 and IL-12.

Also not shown are results in which QS-21 was shown to be more effective than IFA in inducing the regression of the tumors.

The foregoing examples demonstrate a composition comprising an amount of a p53 derived peptide, an adjuvant, e.g., QS-21, and Interleukin-12, as well as the use of the composition in the in vivo treatment of cancer. The immunogen is used in an amount sufficient to provoke an immune response against tumor cells which present it on their surface, and combined with QS-21 and IL-12. Among the noteworthy features of the invention is the fact that none of the peptide, the adjuvant, nor the IL-12 worked to stimulate an immune response when used alone, nor was the response particularly strong when the peptide was combined with adjuvant. Further, the results show that the IL-12 is particularly effective after tumors have already formed, and as combined with the peptide and the adjuvant, is effective in very small does.

The compositions of the invention comprise any peptide or protein, derived from p53, in combination with a pharmaceutically acceptable adjuvant. Preferred embodiments of the invention utilize the peptides of SEQ ID NO: 1 and 2. Other p53 based peptides may also be used.

As will be seen from the foregoing discussion, an important aspect of the invention is stimulation of proliferation of T cells. This can be an initial stimulation or an augmentation of a prior stimulation. In particular, it is desirable to stimulate cytolytic T cells. The cytolytic T cells recognize complexes of MHC and peptide, bind thereto via their receptor, and proliferate. They also lyse the recognized cells. This response can be used not only in vivo, but in vitro, as it is well established that cytolytic T cells specific for particular complexes of MHC and peptide are present in the blood of subjects who have experienced cell transformation. By contacting a blood sample of individuals in vitro with the peptide of interest and cells which present the MHC molecule of interest, any cytolytic T cells in the blood sample will expand, i.e., proliferate. This proliferation an be measured via any of the well known assays designed therefor. Especially preferred are the well known radioactive chromium ($^5$Cr) release assay, and the measurement of release of tumor necrosis factor (TNF). These assays are efficacious when peptides such as mutant p53 peptides and other p53 peptides, are used.

The compositions are also useful as stimulators of B cell proliferation, or antibody production. Again, it is well known that B cells produce antibodies, and the size of their targets are well within the sizes of the p53 antigen. As with T cells, the stimulation may be "ab initio", or an augmentation of a prior response, in vitro or in vivo.

The amount of peptide used will vary, depending upon the purpose of the immunization and the subject to which it is administered. For example, in the case of generating murine antibodies which can then be used, e.g., to diagnose for the presence of cancer cells presenting a p53 peptide, the amount of protein or peptide may be less than that used in a course of in vivo therapy, such as that described in the example, supra. In general, a preferred dose can range from about 1 ug to about 750 ug of protein or peptide per dose. In a preferred embodiment, the range is from about 10 ug to about 500 ug. Most preferably, anywhere from about 30 ug to about 300 ug per dose may be used. Of course, in the context of the therapeutic aspect of the invention, the investigator will modify the dose, as a six month old infant will require dosing different from a full grown man, e.g. The mode of administration may vary, with preferred forms being oral, subcutaneous, intramuscular, intravenous and intraperitoneal administration.

The choice of protein or peptide in the composition will depend upon parameters determinable by the artisan. It is art recognized, for example, that different peptides are presented by the various MHC molecules. As such, if a subject is typed, using well known techniques, as presenting HLA-A2 molecules on the surface of tumor cells, one will use a peptide presented by HLA-A2 molecules rather than one presented by, e.g., HLA-Cw$^*$ 1601. Similarly, using techniques such as polymerase chain reaction ("PCR"), lysis studies, and other assay methodologies which are well known in the art, one can determine which protein or peptide is being expressed by a subject patient. This will lead to the decision as to what protein or peptide to use. Again, by way of example, if a subject's tumor cells are expressing mutant p53 but not normal p53 peptide, the peptide used in immunization should be derived from the mutant form.

Other aspects of the invention will be clear to the skilled artisan and need not be reiterated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Composition useful in provoking an immune response comprising an amount of (i) an immunogenic p53 derived protein or peptide, (ii) an adjuvant, and (iii) interleukin-12, wherein said interleukin-12 is present in an amount of no more than 1 ng per 100 ug of said immunogenic p53 derived protein or peptide, but is present in an amount sufficient to provoke an immune response.

2. The composition of matter of claim 1, wherein said p53 derived protein or peptide binds to an MHC molecule.

3. The composition of claim 1, wherein said immune response is a B cell response.

4. The composition of claim 1, wherein said adjuvant comprises a saponin.

5. The composition of claim 4, wherein said adjuvant comprises QS-21.

6. Method for provoking an immune response in a subject comprising administering to said subject an immune stimulating amount of the composition of claim 1.

7. The method of claim 6, wherein said immune response is a T cell response.

8. The method of claim 6, wherein said adjuvant is QS-21.

9. The method of claim 6, wherein said subject is afflicted with a tumor.

10. Kit useful in provoking an immune response, comprising a container means and a separate portion of each of
    (i) an immunogenic p53 derived protein or peptide,
    (ii) an adjuvant, and
    (iii) interleukin-12, wherein said interleukin-12 is present in an amount of 1 ng or less per 100 ug of (i).

* * * * *